United States Patent [19]

Poli et al.

[11] Patent Number: 5,010,108

[45] Date of Patent: Apr. 23, 1991

[54] N-CYCLOALKYLAMINOETHYLBENZA-MIDE DERIVATIVES, THEIR SYNTHESIS AND PHARMACEUTICAL PREPARATIONS

[75] Inventors: Stefano Poli; Germano Coppi; Lucio Del Corona, all of Milan, Italy

[73] Assignee: Poli Industria Chimica S.p.A., Milan, Italy

[21] Appl. No.: 324,596

[22] Filed: Mar. 15, 1989

[30] Foreign Application Priority Data

Mar. 17, 1988 [IT] Italy .................... 19814 A/88

[51] Int. Cl.$^5$ .................. C07C 237/44; A61K 31/165
[52] U.S. Cl. ..................... 514/619; 514/872; 514/899; 564/197
[58] Field of Search ............ 564/167; 514/619, 872, 514/899

[56] References Cited

U.S. PATENT DOCUMENTS

| | | | |
|---|---|---|---|
| 3,219,528 | 11/1965 | Thominet | 167/65 |
| 3,536,712 | 10/1970 | Keck et al. | 260/253 |
| 3,678,094 | 7/1972 | Shen et al. | 260/471 R |
| 3,833,733 | 9/1974 | Thominet | 424/324 |
| 4,742,083 | 5/1988 | Ritchey | 514/617 |

FOREIGN PATENT DOCUMENTS

| | | |
|---|---|---|
| 0589016 | 12/1959 | Canada . |
| 1272477 | 4/1972 | United Kingdom . |
| 1353331 | 5/1974 | United Kingdom . |
| 2160871 | 1/1986 | United Kingdom . |

*Primary Examiner*—Richard L. Raymond
*Assistant Examiner*—P. O'Sullivan
*Attorney, Agent, or Firm*—Michael J. Striker

[57] ABSTRACT

New N-(2-cycloalkylamino)ethyl-substituted benzamides having a powerful stimulating activity on gastric motility and with a low central anti-dopaminergic activity are described. The synthesis and the pharmaceutical preparation for therapeutical use are also described.

7 Claims, No Drawings

N-CYCLOALKYLAMINOETHYLBENZAMIDE DERIVATIVES, THEIR SYNTHESIS AND PHARMACEUTICAL PREPARATIONS

BACKGROUND OF THE INVENTION

Our invention relates to new N-cycloalkylaminoethylbenzamide derivatives and improved pharmacological preparations derived therefrom.

In Fr-1313758 there is described the 4-amino-5-chloro-N-(2-diethylamino)ethyl)-o-anisamide, also known as metoclopramide, which is a drug that has been used for a considerable time in the therapeutic practice as an antiemetic and gastrokinetic drug. Metoclopramide however shows side-effects at the central nervous system level, that can be attributed to a central antidopaminergic activity.

The compounds of the present invention, besides having a stronger gastrokinetic activity compared to metoclopramide, also exhibit a lower central antidopaminergic activity and a lower toxicity, thus showing higher therapeutic indexes. Thus selective activity in the gastrointestinal tract is unexpected and is related to the presence of N-cycloalkyl group.

More specifically, the compounds: 2-methoxy-4-amino-5-chloro-N-(2-(cyclopropylamino)ethyl)-benzamide (Example 1, compound II) and 2-methoxy-4-amino-5-chloro-N-(2-(methylcyclopropylamino)ethyl)-benzamide (Example 2; compound III) show in the rat gastric emptying time test (Brodie D.A. and Kundrats S.K. Proc., 24, 714, 1965) a markedly higher activity than metoclopramide, that is used as a reference drug.

The dosage levels that increase by 50% the gastric transit rate after 3 hours are as follows II= 0.27 (0.20–0.36) mg/kg, III=0.20 (0.08–0.48) mg/kg and metoclopramide =1.67 (0.95–2.93) mg/kg; the compounds II and III are 6.2 and 8.3 times more active than metoclopramide, respectively.

In the central anti-dopaminegeric activity test, by using apomorphine in rat (Janssen P. A. J., Niemegeers C. J. C., Jagenau A. H. M., Arzneim, Forsch., 10, 1003, 1960). metoclopramide exhibits an $ED_{50}$ of 2.22 (1.43–3.46) mg/kg versus an ED50 of 4.26 (3.72–4.87) mg/kg for II and of 4.76 (3.39–6.67) mg/kg for III. The compounds II and III are 1.9 and 2.1 times less active than the control drug, respectively.

In the cataleptic activity test (Athee L., Buncombe G. Acta Pharmacol. et toxicol., 35, 429, 1974) metoclopramide exhibits an $ED_{50}$ of 43.44 (30.90–61.08) mg/kg versus an $ED_{50}$ of >320 mg/kg for II and of 194.66 (164.32–230.54) mg/kg for III. The compounds II and III are more than 10 and 4.5 times less active on the C.N.S. than metoclopramide respectively.

It is evident that the compounds of the present invention have an increased activity on gastric motility and a markedly lower central anti-dopaminergic activity compared with metoclopramide. Based on these data, the compounds of the invention should have markedly reduced side-effects compared with metoclopramide, such as for example the increase of plasma prolactin levels and extrapyramidal reactions in man.

The compounds of the present invention have a low toxicity, for example the LD50 per os in mouse is about 600 mg/kg as of II, about 1600 mg/kg as of III, that of metoclopramide being of about 350 mg/kg.

The present invention also refers to all the industrial aspects relevant to the use of the compounds of the formula I for the treatment of gastritis, dyspeptic-enterocolitic syndromes, as adjuvants in gastric and duodenal ulcers, biliary diskinesia, gastric troubles caused by drugs, digestion-related headache, headache and digestion-related troubles during the menstrual period and pregnancy, psychosomatic disturbances in anxious subjects, in nausea and vomiting related to slow gastric emptying.

SUMMARY OF THE INVENTION

It is an object of the present invention to provide new aminoethylbenzamide derivatives having improved pharmacological properties, especially relevant to metoclopramide.

In keeping with this object and with others which will become more apparent hereinafter, our invention provides new N-(2-cycloalkylamino)ethyl-substituted benzamides having the formula I

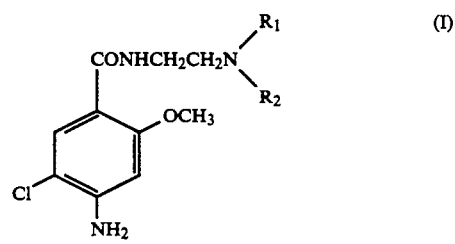

wherein
$R_1$ is H, $C_1$–$C_4$ alkyl, benzyl and
$R_2$ is $C_3$–$C_7$ cycloalkyl.

Advantageously $R_1$ may be hydrogen, methyl, ethyl, isopropyl, benzyl and $R_2$ may be cyclopropyl, cyclopentyl and cyclohexyl.

The solvates and salts of the compounds of the formula I with pharmaceutically acceptable acids are also included in the invention.

The compounds I can be prepared by means of conventional methods, such as they are described for example in the following patents: Fr. 1,407,055, U.S. Pat. No. 3,219,528, G.B. 1,019,781, DE 2,119,724, and by methods using activated esters, and so on. According to a preferred aspect of the invention, the compounds I are prepared by reacting the acid of the formula II with an amine of the formula III in the presence of a condensing agent (dicyclohexylcarbodiimide, carbonyldiimidazole and so on), according to scheme A:

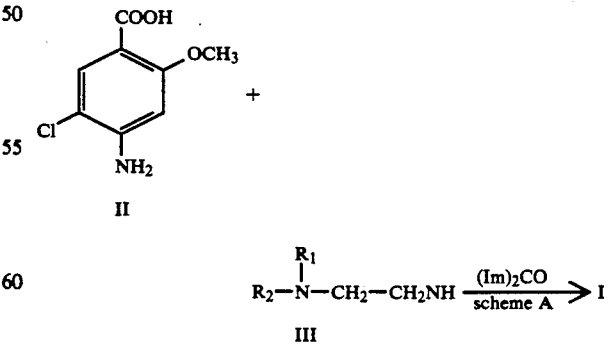

wherein $R_1$ and $R_2$ have the above-mentioned meaning and Im is imidazole.

The above reaction is carried out in solvents such as tetrahydrofuran, DMF, DMSO, acetonitrile, dioxane, at a temperature of from 20° C. to 50° C., the reaction time ranging from 15' to 2 hours. The products are isolated by means of conventional procedures, for example by precipitation from the reaction mixture with water, followed by purification of the product by crystallization from such solvents as alcohols, lower ketones, and so on.

The N,N-cycloalkyl-alkylethylenediamines III of the above reactions are in turn obtained according to scheme B

Scheme B

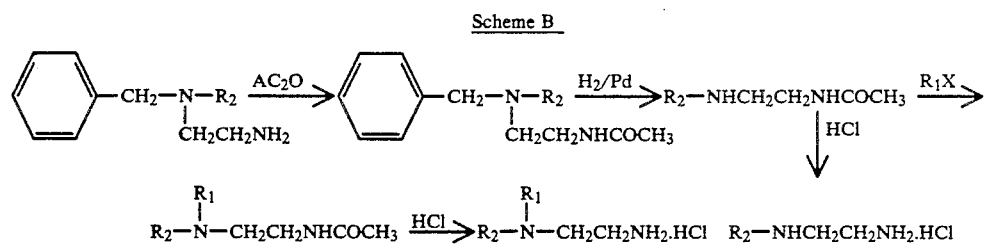

For example, N-benzyl-N-cyclopropylethylenediamine (BE 625,100) is acetylated with acetic anhydride to N-acetyl-N',N'-benzyl-cyclopropylethylenediamine which is then subjected to hydrogenolysis in the presence of palladium supported on carbon to yield N-acetyl-N'-cyclopropylethyleneamine. The latter is hydrolyzed with aqueous mineral acids, for example hydrochloric acid, to cyclopropylethylenediamine or, otherwise, it is alkylated with alkyl halides or sulphates in such solvents as DMF, DMSO, acetone, in the presence of metal alcoholates or alkali carbonates, to N-acetyl-N'-cyclopropyl-N'-alkylethylenediamines which are then saponified with aqueous mineral acids to give the corresponding amines. Otherwise, the compounds I in which $R_1$ H can be obtained in good yield by alkylating I ($R_1$=H) with alkyl halides or sulphates under the same conditions used for the N-acetyl-N'-cycloalkyl-ethylenediamines.

An object of the present invention is therefore to provide pharmaceutical preparation containing the compounds of the formula I, that are suitable for oral and parenteral administration.

Specific, nonlimiting examples of the pharmaceutical preparations according to the present invention are the following ones:

hard and soft gelatin capsules, tablets and sachets containing 1 to 50 mg of active ingredient, i.e. the derivative compounds of formula I, preferably 2 to 10 mg of these compounds, syrups or drops containing 1 to 50 mg of active ingredient, preferably 2 to 10 mg per dosage unit, vials containing 1 to 50 mg, preferably 2 to 10 mg, of active ingredient, in solid form, to be solubilized or suspended in a suitable solvent for parenteral administration.

In the following synthesis details are described but those details must not be considered as limiting, but only as illustrative of the various procedures.

EXAMPLES

EXAMPLE 1 (Compound II)

8.06 g (0.04) mole of 2-methoxy-4-amino-5-chlorobenzoic acid and 7.12 g (0.044 mole) of carbonyldiimidazole are suspended in 80 ml of tetrahydrofuran and kept at 30° C. until the end of gas development. The solution of 5 g (0.05 mole) of cyclopropylethylenediamine in 15 ml of tetrahydrofuran is then slowly added, followed by keeping the temperature at 50° C. for 1 hour. After cooling down, the mixture is poured into water, the solid is removed by filtration and crystallized from alcohol, thus obtaining 13 g (91.7%) of 2-methoxy-4-amino-5-chloro-N-(2-(cyclopropylamino)-ethyl)-benzamide, having a melting point of 152°–3° C. Hydrochloride m.p.

Elementary analysis for $C_{13}H_{18}Cl\ N_3O_2$:

Calcd.: C=55.02%, H =6.39%, N=14.80%, Cl=12.49%.

Found.: C=54.91%, H =6.38%, N=14.69%, Cl=12.40%.

Ir (KBr)$\nu$cm$^{-1}$: 3020 (Str. Δ); 1640 (Str. C=0).

EXAMPLE 2 (Compound III)

19 g (0.1 mole) of N-cyclopropyl-N-benzylethylenediamine are added at 50° C. to 15.3 g (0.15 mole) of acetic anhydride. When the exothermic phase is over, the mixture is kept for further 30 minutes at 70° C., then cooled down and poured into ice. The organic phase is extracted with toluene and, after drying and evaporation, it gives a residue of gas-chromatographically pure N-acetyl-N'-cyclopropyl-N'-benzylethylenediamine with an almost quantitative yield.

This compound is dissolved in 80 ml of ethyl alcohol to which 3.64 g (0.1 mole) of hydrogen chloride gas and 1.5 g of 5% palladium on carbon have been added. The suspension is hydrogenated in about two hours at room temperature. When the hydrogen absorption is ended, the catalyst is removed by filtration, the alcohol is evaporated under vacuum, the residue is taken up with water - potassium carbonate, the solution is extracted with toluene and then evaporated; a chromatographically pure residue of 14.2 g, (100%) of N-acetyl-N'-cyclopropylethylenediamine is obtained.

To a solution of 11.36 g (0.08 mole) of N-acetyl-N'-cyclopropylethylenediamine in 25 ml of DMF, 12.7 g (0.092 mole) of potassium carbonate are added, followed by heating to 50° C. and by further slowly adding 11.6 g (0.092 mole) of dimethyl sulphate. At the end the mixture is kept for further 15 minutes at 80° C., then cooled to room temperature, the DMF is then evaporated at 0.1 mm/Hg, the residue is treated with water-potassium carbonate and extracted with a mixture toluene/ethyl acetate 1/1. After evaporation, 11.4 g (91.3%) of gas-chromatographically pure N-acetyl-N'-methylcyclopropylethylenediamine are obtained.

15.6 g of N-acetyl-N'-methylcyclopropylethylenediamine are refluxed during two hours with 80 ml of 15% hydrochloric acid. The solution is then saturated with sodium hydroxide, extracted with ethyl ether, the organic extract is dried and evaporated at 20° C./15 mm/Hg. Gas-chromatographically pure N-acetyl-N'-methyl-N'-cyclopropylethylene is thus obtained. 8.06 g (0.04 mole) of 2-methoxy-4-amino-5-chlorobenzoic acid and 7.12 g (0.044 mole) of carbonyldiimidazole are suspended in 80 ml of tetrahydrofuran and kept at 30° C. until the gas evolution stopped. A solution containing 5.7 g (0.05 mole) of N-methyl-N-cyclopropylethylenediamine in 15 ml of tetrahydrofuran is then slowly added at room temperature, and thereafter the temperature is kept at 50° C. for one hour. After cooling down, the mixture is poured into water, the solid is removed by filtration and crystallized from alcohol, thus obtaining 9.6 (80.6%) of 2-methoxy-4-amino-5-chloro-N-(2-(methylcyclopropylamino)ethyl-benzamide having a melting point of 164°-5° C. Hydrochloride, m.p. 130°-2° C.

Elementary analysis for $C_{14}H_{20}ClN_3O_2$ Calc.: C=56.46%, H=6.77%, N=14.11%, Cl=11.90%. Found.: C=56.38%, H=6.82%, N=13.99%, Cl=11.85%. IR(KBr) cm$^{-1}$: 3000 (Str. ); 1640(Str. C=0).

In a similar way the products shown in Table I have been prepared.

TABLE I

OTHER NEW N-(2-(CYCLOALKYLAMINO)ETHYL)-SUBSTITUTED BENZAMIDES OF FORMULA (I) PREPARED, THEIR YIELD AND MELTING POINT

| $R_1$ | $R_2$ | Empirical Formula | MW | Yield, % | MP °C. |
|---|---|---|---|---|---|
| —$C_2H_5$ | CP | $C_{15}H_{22}ClN_3O_2$ | 311.8 | 69.0 | 144–6 |
| -i-$C_3H_7$ | CP | $C_{16}H_{24}ClN_3O_2$ | 325.8 | 64.0 | 125–8 |
| —$C_7H_7$ | CP | $C_{20}H_{24}ClN_3O_2$ | 373.8 | 82.5 | 83–5 |

CP = cyclopropyl group

EXAMPLE 3

To a suspension of 2.83 g (0.01 mole) of 2-methoxy-4-amino-5-chloro-N-((2-cyclopropylamino)-ethyl)-benzamide and 1.51 g of potassium carbonate in 20 ml of DMF 1.38 g (0.011 mole) of dimethyl sulphate are slowly added at 50° C. After addition the mixture is kept at 80° C. for 15 minutes, cooled down, poured into water, the solid is removed by filtration and crystallized form ethanol, thus obtained 2.35 g (79%) of 2-methoxy-4-amino-5-chloro-N-(2-(methylcyclopropylamino)ethyl)-benzamide, m.p. 164°-5° C., which is identical with the product obtained in example 2.

We claim:

1. A N-cycloalkylaminoethylbenzamide derivative having the formula I

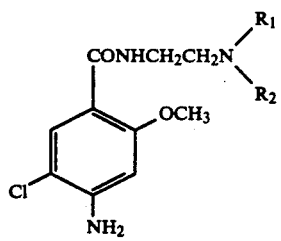

wherein $R_1$ is selected from the group consisting of H and $C_1$-$C_4$ alkyl groups and $R_2$ is cyclopropyl, or a pharmaceutically acceptable salt thereof.

2. A N-cycloalkylaminoethylbenzamide derivative having the formula I

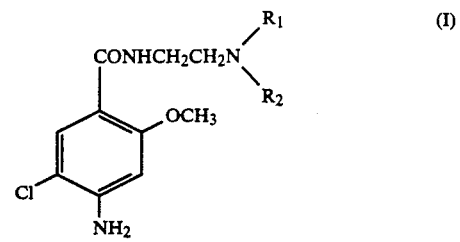

wherein $R_1$ is selected from the group consisting of H, —$CH_3$

—$C_2H_5$, and i—$C_3H_7$; and $R_2$ is cyclopropyl, or a pharmaceutically acceptable salt thereof.

3. A N-cycloalkylaminoethylbenzamide derivative having the formula I

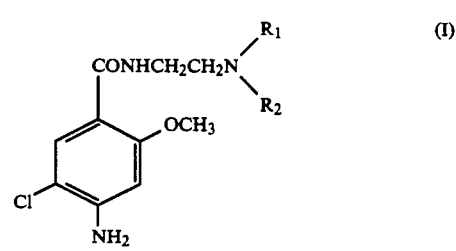

wherein $R_1$ is —$CH_3$ and $R_2$ is cyclopropyl, or a pharmaceutically acceptable salt thereof.

4. A pharmaceutical composition for the treatment of gastritis, gastric trouble, digestion-related headache, digestive problems to menstruation and pregnancy, psychosomatic disturbance in anxious subjects, nausea and vomiting related to slow gastric elimination comprising an effective amount of an N-cycloalkylaminoethylbenzamide derivative selected from the group consisting of -benzamide and 2-methoxy -4-amino-5-chloro-N-2-methoxy-4-amino-5-chloro-N-(2-(cyclopropylamino)- ethyl)-benzamide and 2-methoxy-4-amino-5-chloro-N-(2-(methylcyclopropylamino)-ethyl)-benzamide as the active ingredient in hard and soft gelatin capsules, tablets, drops syrups and vials.

5. A pharmaceutical composition according to claim 4, containing from about 1 to 50 mg of said active ingredient.

6. A pharmaceutical composition according to claim 4, containing from about 2 to 10 mg of said active ingredient.

7. A method of treating gastritis, gastric trouble, digestion-related headache, digestive problems related to menstruation and pregnancy, psychosomatic disturbance in anxious subjects, nausea and vomiting related to slow gastric elimination comprising systematically administering a pharmaceutically effective amount of said N-cycloalkylaminoethylbenzamide derivative according to claim 2.

* * * * *